United States Patent
Koshimura

(10) Patent No.: US 9,863,872 B2
(45) Date of Patent: Jan. 9, 2018

(54) SAMPLE ANALYZER AND METHOD OF SELECTING ANALYSIS REGIONS OF NOISE AFFECTED TIME SERIES DATA FOR A TARGET REACTION

(71) Applicant: SYSMEX CORPORATION, Kobe-shi, Hyogo (JP)

(72) Inventor: Naoto Koshimura, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 4 days.

(21) Appl. No.: 15/080,129

(22) Filed: Mar. 24, 2016

(65) Prior Publication Data
US 2016/0291040 A1 Oct. 6, 2016

(30) Foreign Application Priority Data
Mar. 31, 2015 (JP) ................. 2015-072807

(51) Int. Cl.
*G01N 33/86* (2006.01)
*G01N 21/27* (2006.01)
(Continued)

(52) U.S. Cl.
CPC ........... *G01N 21/272* (2013.01); *G01N 21/82* (2013.01); *G01N 33/4905* (2013.01);
(Continued)

(58) Field of Classification Search
CPC ......... G01N 33/86; G01N 21/27; G01N 21/35
(Continued)

(56) References Cited

U.S. PATENT DOCUMENTS 5,526,111 A * 6/1996 Collins .............. G01N 33/4905
128/DIG. 22
5,793,380 A 8/1998 Matsuno
(Continued)

FOREIGN PATENT DOCUMENTS

JP 2004-347385 * 12/2004
JP 2007-065883 * 3/2007
(Continued)

OTHER PUBLICATIONS

Zhu, L. et al, SPIE 2011, 7997, paper 799721, 6 pages.*
Lipi, G. et al, Journal of Laboratory Automation 2013, 18, 382-390.*

*Primary Examiner* — Arlen Soderquist
(74) *Attorney, Agent, or Firm* — Metrolexis Law Group, PLLC

(57) ABSTRACT

A sample analyzer includes: a preparation unit configured to mix a sample with a reagent to prepare a measurement specimen; a measurement unit configured to irradiate the measurement specimen with light to acquire optical time series data; and a controller configured to divide the time series data acquired by the measurement unit into data segments, determine first regression lines respectively of the data segments, select the first regression line with the highest matching degree with the time series data, set as an analysis target region a region of the time series data matching with the selected first regression line among the time series data acquired by the measurement unit, determine a second regression line using the time series data included in the set analysis target region, and perform an analysis using the second regression line.

20 Claims, 16 Drawing Sheets

(51) Int. Cl.
*G01N 21/35* (2014.01)
*G01N 33/49* (2006.01)
*G01N 21/82* (2006.01)
*G01N 35/00* (2006.01)

(52) U.S. Cl.
CPC . *G01N 35/00584* (2013.01); *G01N 2021/825* (2013.01); *G01N 2035/0097* (2013.01); *G01N 2035/00465* (2013.01)

(58) Field of Classification Search
USPC .................. 422/63–67, 73; 436/43, 47, 69; 700/266; 702/19, 22–23, 25, 30, 32
See application file for complete search history.

(56) References Cited

U.S. PATENT DOCUMENTS

| | | | | |
|---|---|---|---|---|
| 6,524,861 B1* | 2/2003 | Anderson | ............. | G01N 33/86 422/63 |
| 8,507,281 B2* | 8/2013 | Lee | ............. | A61B 5/14532 422/82.05 |
| 9,581,609 B2* | 2/2017 | Yabutani | ............. | G01N 33/86 |
| 2010/0235103 A1* | 9/2010 | Carroll | ............. | G01N 21/82 702/19 |
| 2012/0064636 A1 | 3/2012 | Mitsuyama et al. | | |
| 2012/0288409 A1* | 11/2012 | Inabe | ............. | G01N 21/51 422/82.05 |
| 2014/0255254 A1 | 9/2014 | Yamaguchi et al. | | |
| 2015/0316531 A1 | 11/2015 | Tarumi et al. | | |
| 2016/0066978 A1* | 3/2016 | Keller | ............. | A61B 18/14 606/40 |
| 2016/0291046 A1* | 10/2016 | Yabutani | ............. | G01N 33/86 |

FOREIGN PATENT DOCUMENTS

| | | |
|---|---|---|
| JP | 2013-089112 A | 5/2013 |
| JP | 2014-106032 A | 6/2014 |

\* cited by examiner

FIRST WAVELENGTH (800 nm)

SECOND WAVELENGTH (405 nm)

SAMPLE ANALYZER AND METHOD OF SELECTING ANALYSIS REGIONS OF NOISE AFFECTED TIME SERIES DATA FOR A TARGET REACTION

CROSS REFERENCE TO RELATED APPLICATIONS

This application claims priority based on 35 USC 119 from prior Japanese Patent Application No. 2015-072807 filed on Mar. 31, 2015, entitled "SAMPLE ANALYZER, SAMPLE ANALYZING METHOD, AND COMPUTER PROGRAM", the entire contents of which are hereby incorporated by reference.

BACKGROUND

The disclosure relates to a sample analyzer, a sample analyzing method, and a computer program.

There is known a blood coagulation analyzer configured to conduct a blood coagulation test by analyzing time series data optically acquired from a measurement specimen which is a mixture of a sample with a reagent. Such time series data acquired with the blood coagulation analyzer sometimes includes abnormal data due to air bubbles or the like in a measurement specimen.

Japanese Patent Application Publication No. 2014-106032 (hereinafter, Patent Literature 1) discloses a technique in a blood coagulation analyzer of approximating optically acquired time series data using an approximated curve, and removing abnormal data (noise) departing from the approximated curve.

The blood coagulation analyzer described in Patent Literature 1 obtains an approximated curve of time series data including a noise, and removes the noise using the approximated curve. Hence, the approximated curve itself includes an inaccuracy which may adversely influence the reliability of the analysis result.

In addition, a graph drawn using time series data optically acquired with the blood coagulation analyzer varies in shape depending on the measurement principle, reagents, and so forth. For this reason, to perform a highly reliable analysis in a blood coagulation test, some modification has to be made to reduce an influence of abnormal data in accordance with the shape of a graph obtained from time series data.

SUMMARY

An embodiment of a sample analyzer comprises a preparation unit that mixes a sample with a reagent to prepare a measurement specimen, a measurement unit that irradiates the measurement specimen with light to acquire optical time series data, a controller that divides the time series data acquired by the measurement unit into data segments, determines first regression lines respectively of the data segments, select the first regression line with the highest matching degree with the time series data, sets as an analysis target region a region of the time series data matching with the selected first regression line among the time series data acquired by the measurement unit, determines a second regression line using the time series data included in the set analysis target region, and analyzes using the second regression line.

An embodiment of a sample analyzing method comprises mixing a sample with a reagent to prepare a measurement specimen, irradiating the measurement specimen with light to acquire optical time series data, dividing the acquired the time series data into data segments, determining first regression lines respectively of the data segments, selecting the first regression line with the highest matching degree with the time series data, setting as an analysis target region a region of the time series data matching with the selected first regression line among the acquired time series data, determining a second regression line using the time series data included in the set analysis target region, and performing an analysis using the second regression line.

An embodiment of a computer program executed in a sample analyzer including a measurement unit that irradiates with light a measurement specimen prepared by mixing a sample with a reagent to acquire optical time series data, the computer program enabling the sample analyzer to function as: a selector that divides the time series data acquired by the measurement unit into data segments, determine first regression lines respectively of the data segments, and selects the first regression line with the highest matching degree with the time series data, and an analyzer that sets as an analysis target region a region of the time series data matching with the selected first regression line among the time series data acquired by the measurement unit, determines a second regression line using the time series data included in the set analysis target region, and analyzes using the second regression line.

EMBODIMENTS

First Embodiment

A sample analyzer according to the first embodiment is a blood coagulation analyzer. The blood coagulation analyzer performs an analysis regarding blood coagulability by irradiating with light a measurement specimen prepared by mixing a blood sample with a reagent, and by analyzing an acquired optical measurement signal according to a coagulation method, a synthetic substrate method, immunonephelometry, and an agglutination method. Hereinafter, description is given particularly of a measurement of Factor VIII according to the synthetic substrate method.

Figure 1:
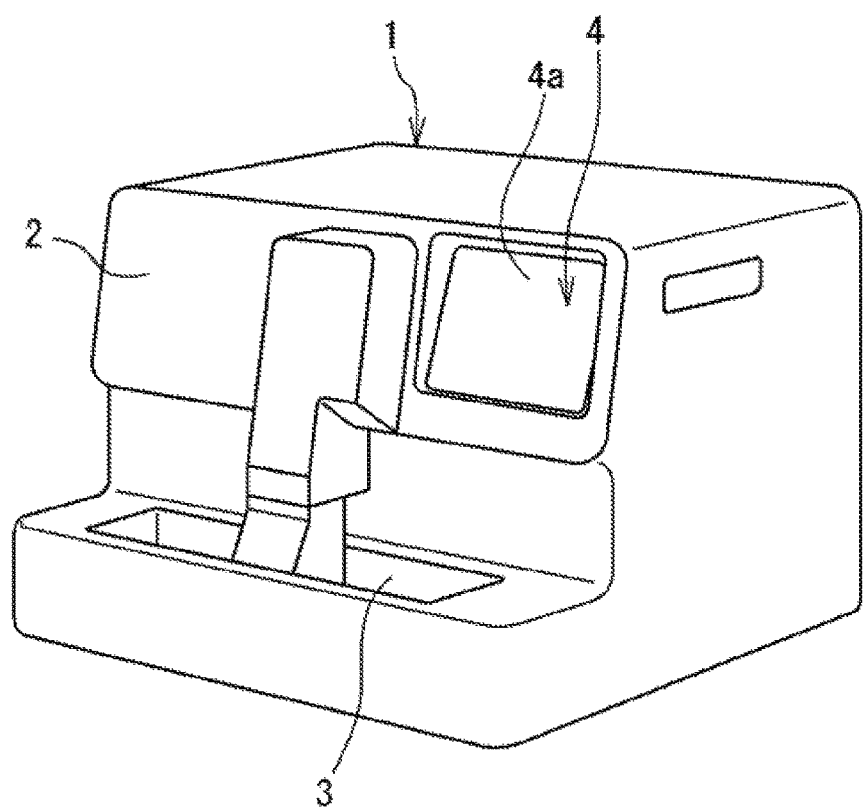
FIG. 1 is a perspective view of a sample analyzer according to a first embodiment.

As illustrated in FIG. 1, blood coagulation analyzer 1 includes measurement device 2 configured to optically measure a measurement specimen including a blood sample such as plasma, sample transporting apparatus 3 disposed in front of measurement device 2 and configured to transport a sample container containing a blood sample, and control device 4 configured to analyze measurement data acquired by measurement device 2 and to provide an instruction to measurement device 2.

Figure 2:
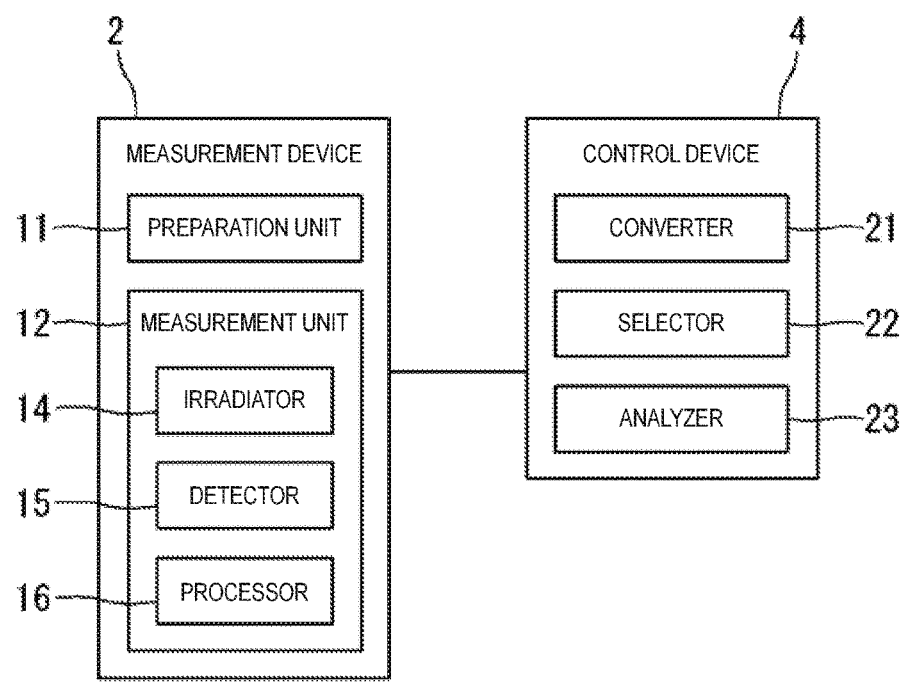
FIG. 2 is a block diagram of the sample analyzer.

As illustrated in FIG. 2, measurement device 2 includes preparation unit 11 and measurement unit 12. Preparation unit 11 is configured to dispense a blood sample in the sample container transported by sample transporting apparatus 3 and a reagent in a reagent container set in measurement device 2 into a reaction chamber to prepare a measurement specimen by stirring, heating, and so forth. The measurement specimen is transported to measurement unit 12. Measurement unit 12 is configured to perform an optical measurement.

Measurement unit 12 includes irradiator 14 having a light source such as a halogen lamp or an LED, detector 15 having a light receptor such as a photodiode, processor 16 including a CPU, a memory, and so on. Irradiator 14 is configured to irradiate a measurement specimen with predetermined light. Irradiator 14 of the first embodiment is configured to irradiate a measurement specimen with light at multiple wavelengths. For example, irradiator 14 uses a filter to disperse light at a wavelength of 405 nm and light at a wavelength of 800 nm and irradiates the measurement specimen with the light. Irradiator 14 emits the light at a wavelength of 405 nm and the light at a wavelength of 800 nm a predetermined time. For example, irradiator 14 emits the light at each wavelength every 0.1 seconds.

Detector 15 is configured to receive light from a measurement specimen and output an electrical signal according to the amount of light received. Particularly, detector 15 is configured to receive transmitted light, scattered light, fluorescent light, or the like from a measurement specimen. In the synthetic substrate method employed to blood coagulation analyzer 1 of the present embodiment, irradiator 14 irradiates a measurement specimen with light at a wavelength of 405 nm, and detector 15 receives transmitted light from the measurement specimen. As a coagulation reaction of the measurement specimen proceeds, the turbidity of the measurement specimen increases, and the amount of the transmitted light received by detector 15 decreases, so that the output level of the electrical signal is decreased.

Irradiator 14 is configured to irradiate a measurement specimen with light at a wavelength of 800 nm, too, and detector 15 is configured to receive transmitted light from the measurement specimen. In measuring Factor VIII according to the synthetic substrate method, light at a wavelength of 800 nm is not reflected in the coagulation reaction of a measurement specimen, and the amount of transmitted light hardly changes. An electrical signal that detector 15 outputs in response to light at a wavelength of 800 nm is mainly utilized to acquire data other than a noise as described later.

Processor 16 of measurement unit 12 is configured to convert an electrical signal of transmitted light detected by detector 15 to digital data. Moreover, processor 16 is configured to transmit the converted digital data to control device 4.

In measurement unit 12, a measurement specimen is irradiated with light at a wavelength of 405 nm and light at a wavelength of 800 nm for a predetermined time in a single measurement. Digital data on the amount of transmitted light during this event is acquired as time series data. For example, in a single measurement, a measurement specimen is irradiated with light at each wavelength for 25 seconds. Moreover, in a case where a measurement specimen is irradiated with light at each wavelength every 0.1 seconds, time series data is also acquired every 0.1 seconds. Thus, during the irradiation for 25 seconds in a single measurement, 250 pieces of time series data are acquired for the light at each wavelength.

Control device 4 includes a controller, a storage, display 4a (see FIG. 1), and so forth. The controller includes a CPU, and a storage including a ROM, a RAM, and the like. The controller is configured to cause the CPU to execute a computer program stored in the storage and perform predetermined functions. The controller of the present embodiment performs functions as converter 21, selector 22, and analyzer 23 as illustrated in FIG. 2. The controller is configured to receive time series data on the amount of transmitted light, which is an optical measurement signal transmitted from processor 16 of measurement unit 12.

Figure 3:
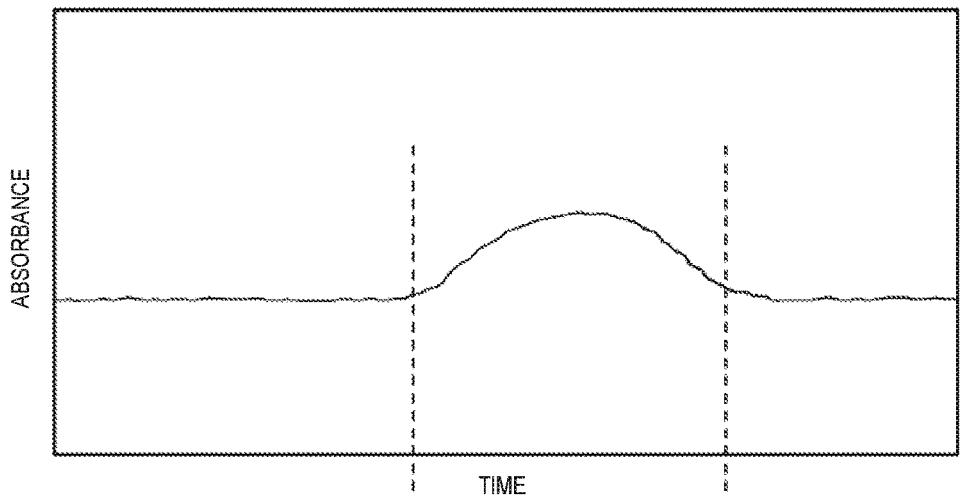
FIG. 3 illustrates graphs for illustrating time series data on two types of wavelengths.
Figure 3:
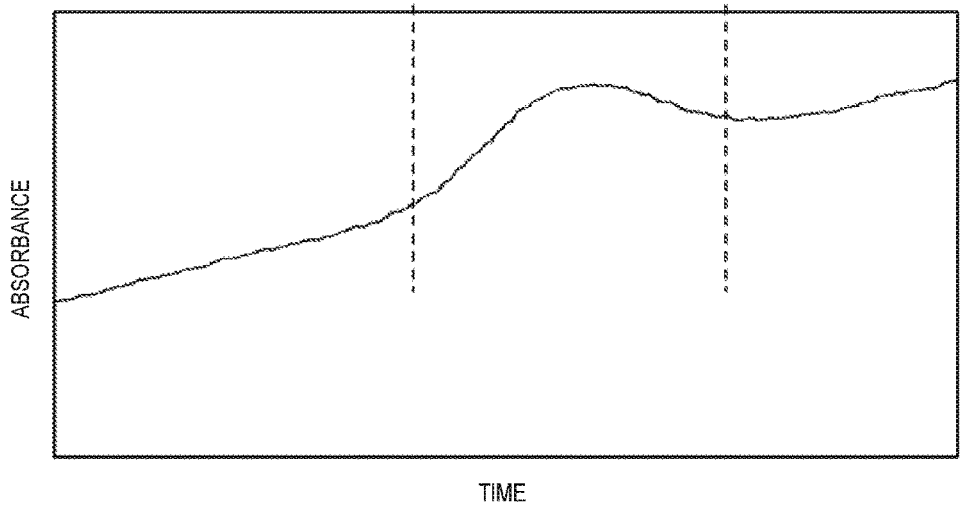

Converter 21 of control device 4 is configured to convert time series data on the "amount of transmitted light" inputted from measurement unit 12 to time series data on the "absorbance". FIG. 3 illustrates changes over time of time series data after the conversion in graphs. In FIG. 3, a first wavelength is 800 nm, and a second wavelength is 405 nm. The maximum value of the time in the horizontal axis is 25 seconds which is the time in a single measurement. In both of the time series data, the absorbance is increased in a certain segment due to a noise.

In the time series data on the first wavelength, the absorbance hardly changes and takes a substantially constant value except for the noise. In other words, the time series data on the first wavelength is data not reflecting the progression of blood coagulation, but reflecting only the noise. This noise is caused by bubbles, aggregate lumps, or the like generated in the measurement specimen. When bubbles or aggregate lumps enter a region irradiated with light by irradiator 14, the absorbance is gradually increased. Meanwhile, when bubbles or aggregate lumps disappear from the region, the absorbance is gradually decreased. The length of a segment when this noise appears is approximately 10 seconds.

In the time series data on the second wavelength, the absorbance is increased almost in proportion to the time except for the noise. This indicates that the time series data on the second wavelength is data reflecting a blood coagulation reaction. In the second wavelength also, the increase in the absorbance due to the noise is observed in the same segment as that in the first wavelength.

Selector 22 of control device 4 is configured to specify a region with no noise by using the time series data on the first wavelength, and to set this region as an "analysis target region." Meanwhile, analyzer 23 of control device 4 is configured to apply the analysis target region specified by selector 22 to the time series data on the second wavelength, and perform an analysis related to coagulability in the analysis target region. Hereinafter, specific processings of selector 22 and analyzer 23 are described using FIGS. 4 to 7 and a flowchart of FIG. 8. The flowchart of FIG. 8 separately illustrates the processing of selector 22 for the time series data on the first wavelength and the processing of analyzer 23 for the time series data on the second wavelength.

Figure 4:
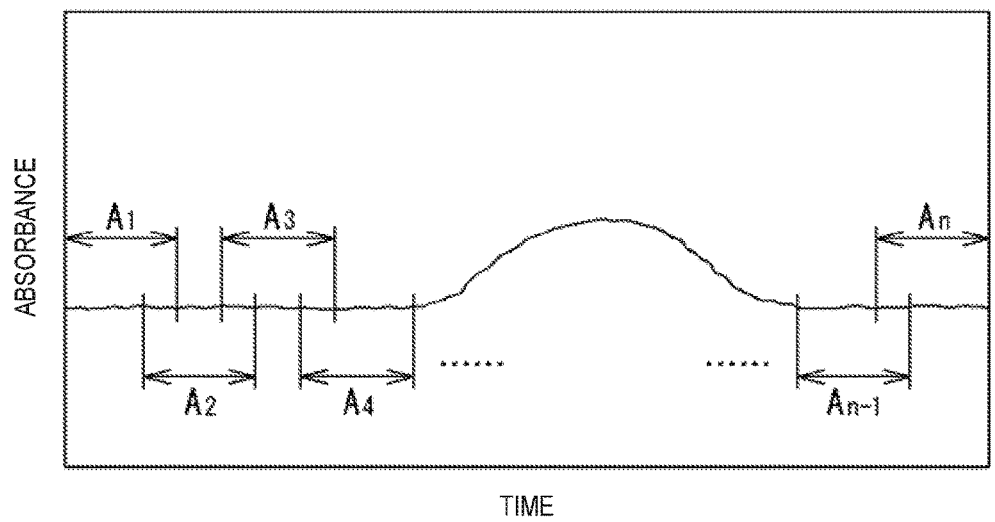
FIG. 4 is a graph for explaining an example of dividing the time series data into data segments.
Figure 8:
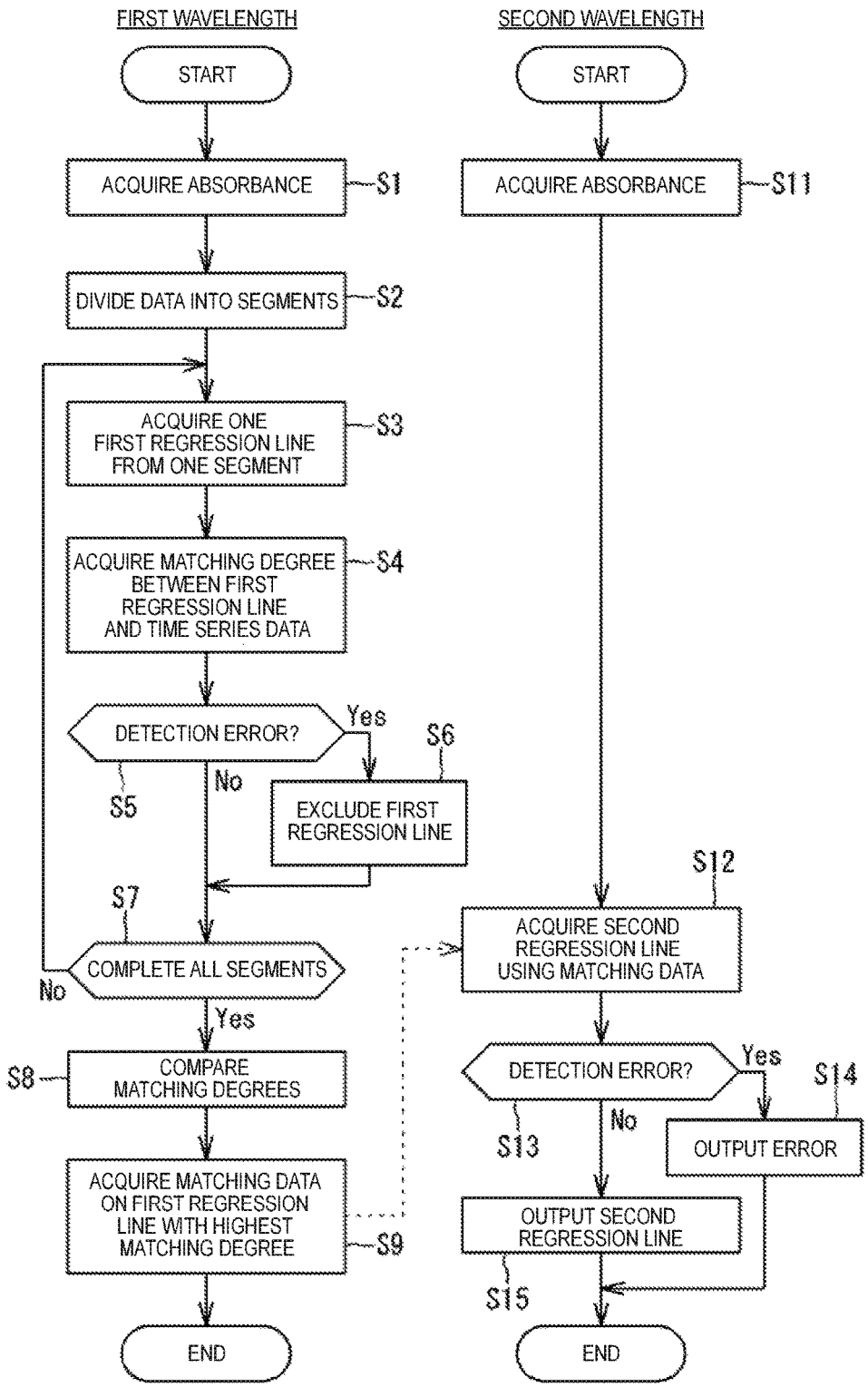
FIG. 8 is a flowchart for illustrating a process procedure of a control device.

In step S1 of FIG. 8, converter 21 of control device 4 converts time series data on the "amount of transmitted light" transmitted from measurement device 2 to time series data on the "absorbance". Next, in step S2, selector 22 of control device 4 divides a period of acquiring the time series data on the first wavelength into segments An (n is an integer of 1 or more) as illustrated in FIG. 4.

The length of each segment An may be between 1/10 and 1/3 of the period of acquiring the time series data. Here, the length of segment An is shorter than 25 seconds which is the period of acquiring the time series data, and may be 2.5 seconds or longer but shorter than 8.3 seconds. This length is set, for example, 5 seconds. Thus, the number of data included in segment An is 50. Hereinbelow, the data included in each segment An is referred to as a data segment, and distinguished from the entire time series data. The length of segment An is shorter than a time when a noise is generated. Segments An have portions overlapping each other. Segments An next to each other preferably overlap each other by 50% or more in consideration of precision, and preferably by less than 80% in consideration of measurement time. For example, segments An next to each other overlap each other for 3 seconds. Thus, 30 pieces of data overlap between segments An next to each other.

Figure 5:
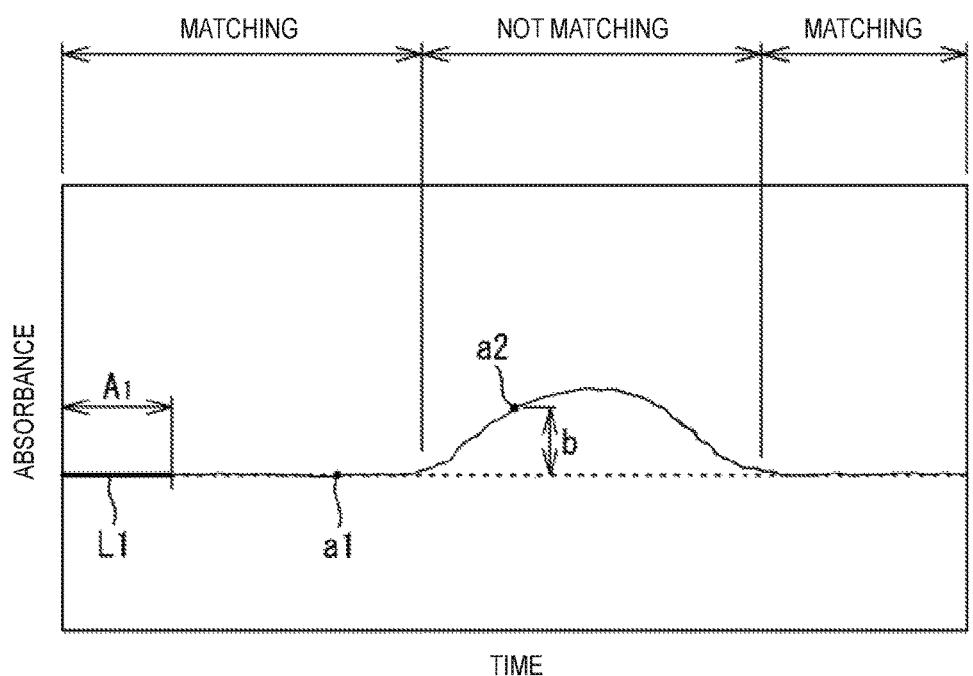
FIG. 5 is a graph for illustrating a first regression line approximated to a data segment.

Next, in step S3 of FIG. 8, selector 22 of control device 4 determines a first regression line approximating to a data segment. In FIG. 5, first regression line L1 of a data segment in segment A1 is illustrated by the solid line. This first regression line L1 is a regression line approximating to the data segment, which is determined, for example, by the least-squares method or the like.

Selector 22 extends first regression line L1 all over the period of acquiring the time series data, as illustrated by the dashed line in FIG. 5. Then, in step S4 of FIG. 8, selector 22 determines a "matching degree" between the time series data and first regression line L1. A matching degree is determined from the number of such data that a difference between the time series data and first regression line L1 is equal to or less than a predetermined threshold. For example, as illustrated in FIG. 5, one piece of time series data a1 matches with first regression line L1, and a difference therebetween is equal to or less than the predetermined threshold. Such time series data a1 is employed for the matching degree calculation. Another time series data a2 has large difference b from first regression line L1, and difference b is more than the predetermined threshold. Thus, this time series data a2 is excluded from the matching degree calculation. A matching degree may be determined from a length of a time including such data that the difference from first regression line L1 is equal to or less than the predetermined threshold. Alternatively, a matching degree may be determined from a percentage of the length of the time including such data relative to the period of acquiring the time series data that the difference from first regression line L1 is equal to or less than the predetermined threshold.

Next, in step S5 of FIG. 8, selector 22 performs a detection error determination on the basis of a relation between first regression line L1 and the time series data. Specifically, as a result of determining the matching degree between the time series data and first regression line L1, in a case where there is negative difference region R, that is, region R of time series data where the absorbance is lower than that of first regression line L1 as illustrated by a hatched area in FIG. 9 and the area of region R is equal to or more than a predetermined threshold, selector 22 excludes such first regression line L1 as a detection error.

Figure 9:
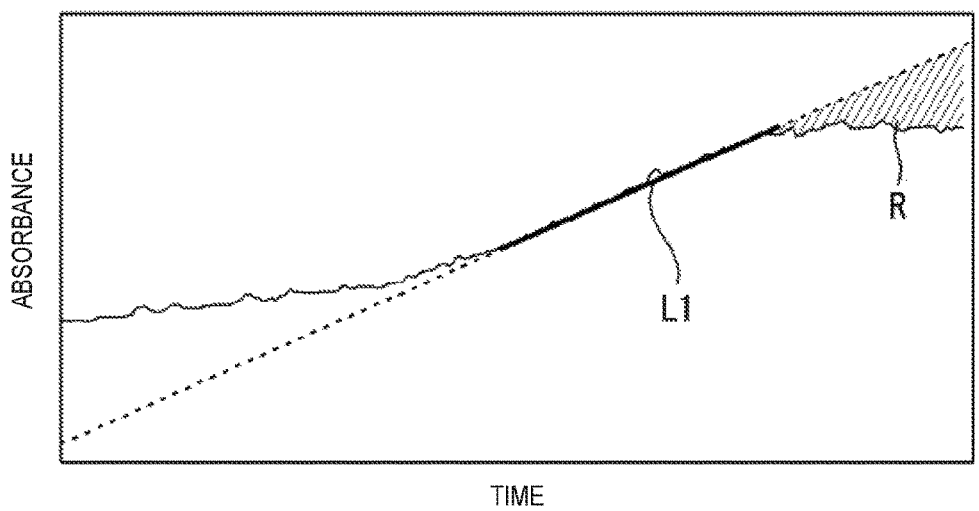
FIG. 9 is a graph for exemplifying a detection error determination condition.

If the difference between first regression line L1 and the time series data is large, it is conceivable that the time series data includes a noise. Nevertheless, in such a case, the time series data including a noise should have a value higher than that of first regression line L1. However, in the example illustrated in FIG. 9, the value of the time series data is lower than that of first regression line L1, first regression line L1 is conceivably approximated to a noise. If a matching degree is high between first regression line L1 approximated to a noise and the time series data, it is not preferable to employ such first regression line L1 to determine an analysis target region to be described later. Thus, at the stage of step S5, if the area of region R illustrated by the hatched area in FIG. 9 is equal to or more than the predetermined threshold, selector 22 determines that first regression line L1 is a detection error, and excludes such first regression line L1 in step S6 of FIG. 8.

In step S7, selector 22 determines whether or not the processings of steps S3 to S6 are completed for all segments An. If the processings are not completed for all segments An, the processings of steps S3 to S6 are repeated. If the processings are completed for all segments An, the processing proceeds to step S8.

Figure 6:
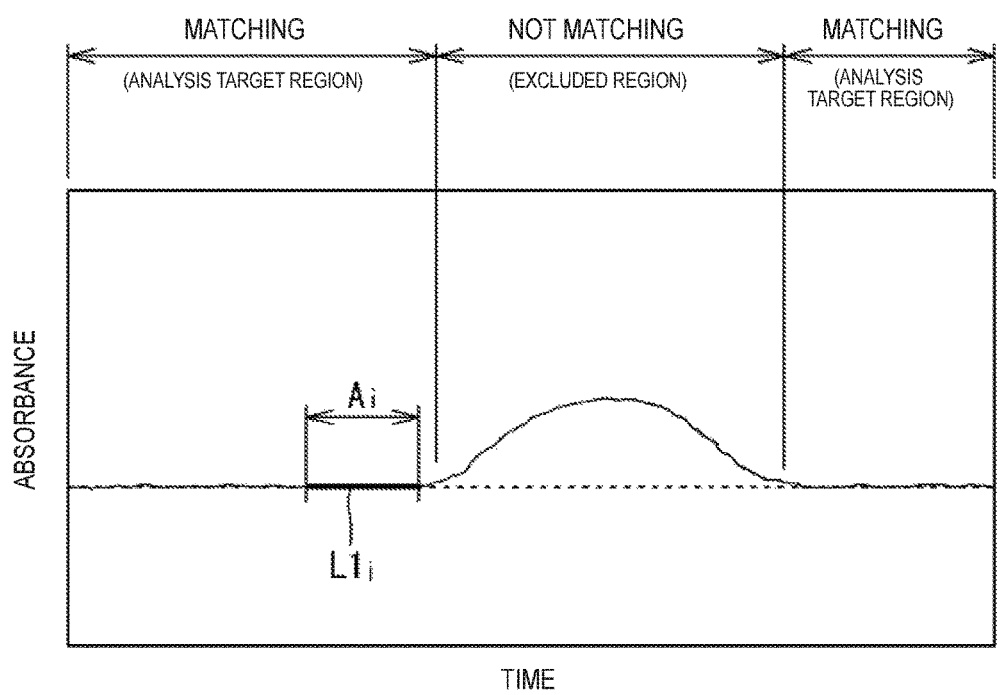
FIG. 6 is a graph for illustrating a first regression line with the highest matching degree.

In step S8, selector 22 compares all segments An with each other in terms of the matching degree with first regression line L1. Then, in step S9, selector 22 selects first regression line L1i of segment Ai with the highest matching degree as illustrated in FIG. 6, and acquires time series data matching with first regression line L1i. Here, the term "match" means not only a case where first regression line L1i completely matches with the time series data, but also a case where a difference between the two is equal to or less than a predetermined threshold. The threshold in this case may be the same as or different from the threshold used in the matching degree calculation.

Analyzer 23 of control device 4 performs an analysis such that a region including the time series data matching with first regression line L1i is set as an "analysis target region." FIG. 6 illustrates regions where first regression line L1 of segment Ai with the highest matching degree matches with the time series data, and a region where the line does not. The matching regions are the analysis target region.

In step S11 of FIG. 8, converter 21 of control device 4 (see FIG. 2) converts the time series data on the amount of transmitted light at the second wavelength transmitted from measurement device 2 to time series data on absorbance. The time series data on the absorbance at the second wavelength is illustrated at the bottom of FIG. 3.

Figure 7:
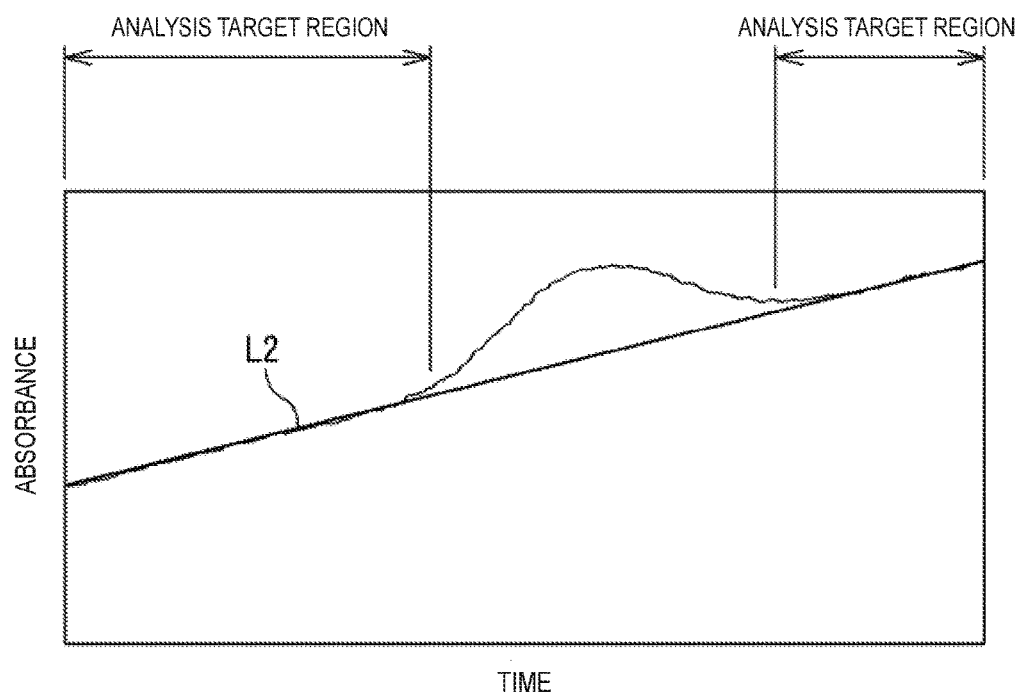
FIG. 7 is a graph for illustrating a second regression line approximated to the time series data.

In step S12 of FIG. 8, analyzer 23 of control device 4 applies the analysis target region (see FIG. 6) determined by selector 22 to the time series data on the second wavelength, and acquires second regression line L2 approximating to the time series data on the analysis target region as illustrated in FIG. 7. This second regression line L2 can be created by the least-squares method or the like.

Figure 10:
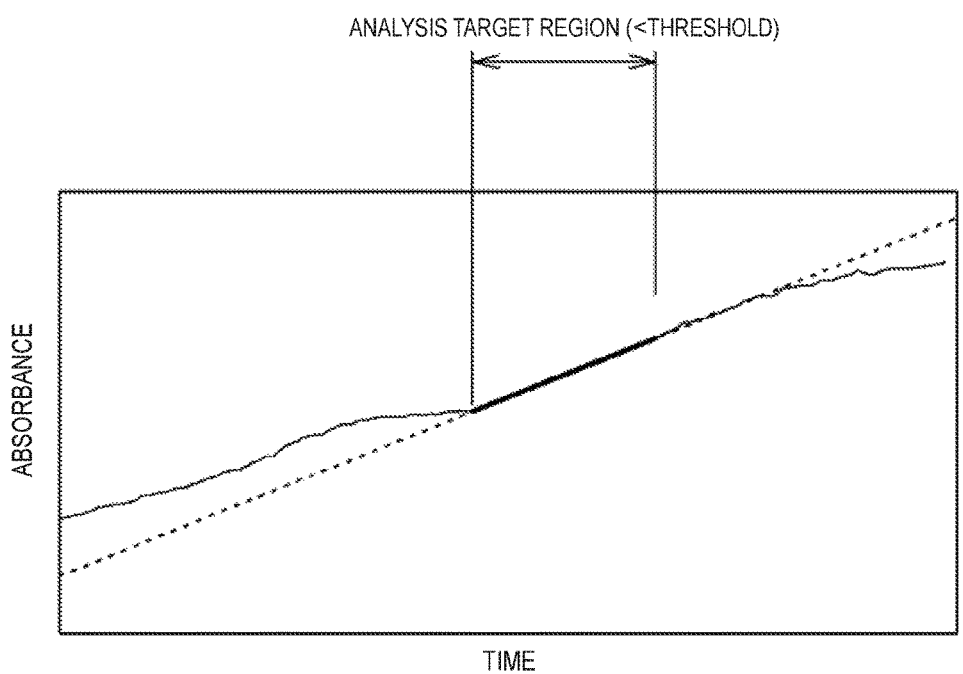
FIG. 10 is a graph for exemplifying a detection error determination condition.

In step S13 of FIG. 8, analyzer 23 determines whether or not the time series data on the absorbance is a detection error. If a width of the analysis target region is equal to or less than a predetermined threshold as illustrated in FIG. 10, analyzer 23 determines a detection error. In this case, it is conceivable that the time series data on the absorbance includes quite a lot of noises. Hence, analyzer 23 determines that the time series data is a detection error, and excludes the time series data. The "width" of the analysis target region compared with the predetermined threshold may be the number of time series data included in the analysis target region, or may be a width of a time of the analysis target region.

If analyzer 23 determines that the time series data is a detection error in step S13 of FIG. 8, analyzer 23 outputs an error on display 4a of control device 4. Meanwhile, if analyzer 23 determines that the time series data is not a detection error in step S13, analyzer 23 outputs a measurement result acquired from second regression line L2, for example, a measurement result regarding a coagulation reaction rate acquired from a slope of second regression line L2, on display 4a of control device 4.

In the embodiment described above, time series data is divided into data segments; first regression lines L1 are determined respectively for the data segments; among first regression lines L1, first regression line L1 with the highest matching degree with the time series data is selected; and a region of the time series data matching with this first regression line L1 is set as the analysis target region. This makes it possible to create second regression line L2 by targeting the region from which a noise is excluded, and to analyze a coagulation reaction state. Hence, a highly reliable analysis can be performed.

Moreover, since first regression lines L1 are determined using data segments divided from time series data, many first regression lines L1 including no noise can be obtained, and it is possible to contribute to setting of more accurate analysis target regions.

In the above embodiment, first regression lines L1 are determined from the time series data on the absorbance at the first wavelength not reflecting coagulation reaction and taking a substantially constant value. Hence, the variation of the time series data is small in regions other than a noise, increasing the matching degree between first regression line L1 and the time series data. This makes it possible to determine a wider analysis target region in a range including no noise, and to determine more accurate second regression line L2.

In the first embodiment, time series data is divided into segments An so as to determine first regression lines L1, and segments An next to each other overlap each other. This makes it possible to divide the period of acquiring the time series data into a larger number of segments An, and to determine first regression line L1 with a higher matching degree.

First regression line L1 and second regression line L2 of the first embodiment are straight lines expressed by a zero polynomial or a monomial. Nevertheless, when time series data is expressed by a curve, for example, as in a case of a high concentration sample, first regression line L1 and second regression line L2 may also be curves expressed by a binomial. It is also possible to express first regression line L1 and second regression line L2 by a polynomial.

Second Embodiment

The first embodiment uses light at two wavelengths of the first wavelength and the second wavelength to acquire time series data thereon. Meanwhile, a second embodiment acquires only time series data on the second wavelength.

Figure 11:
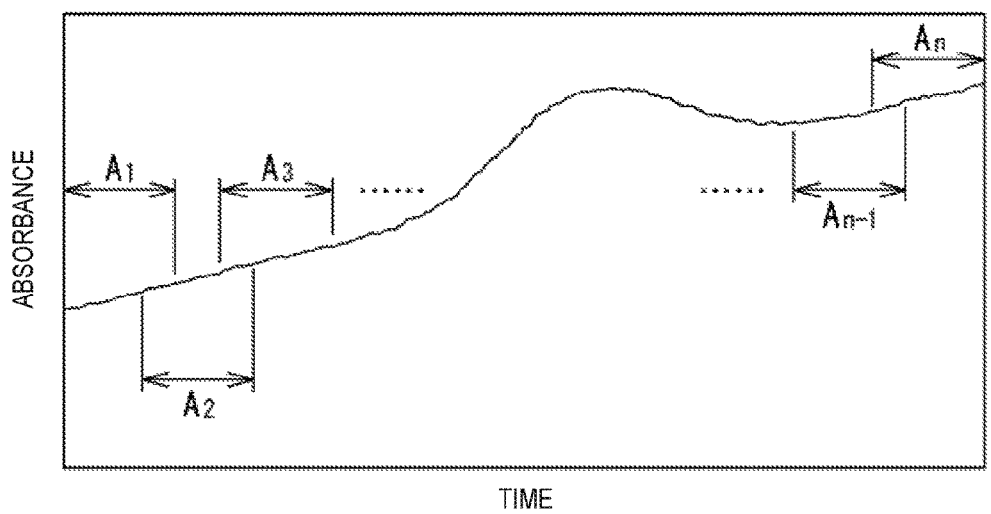
FIG. 11 is a graph for explaining an example of dividing time series data into data segments in a sample analyzer according to a second embodiment.

FIG. 11 illustrates time series data on the absorbance in the second embodiment. This time series data is the same as the time series data illustrated at the bottom of FIG. 3. In this time series data, the absorbance is gradually increased in proportion to the time, and a blood coagulation reaction is reflected. Hereinafter, the second embodiment is described using graphs of FIGS. 11 to 13 and a flowchart illustrated in FIG. 14.

Figure 12:
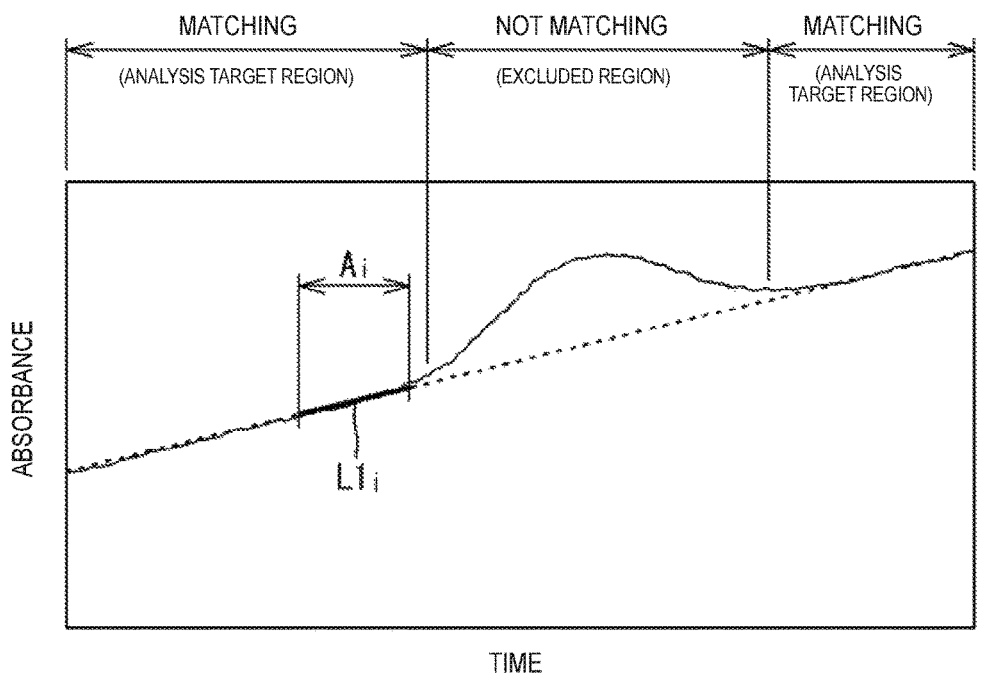
FIG. 12 is a graph for illustrating a first regression line with the highest matching degree.
Figure 14:
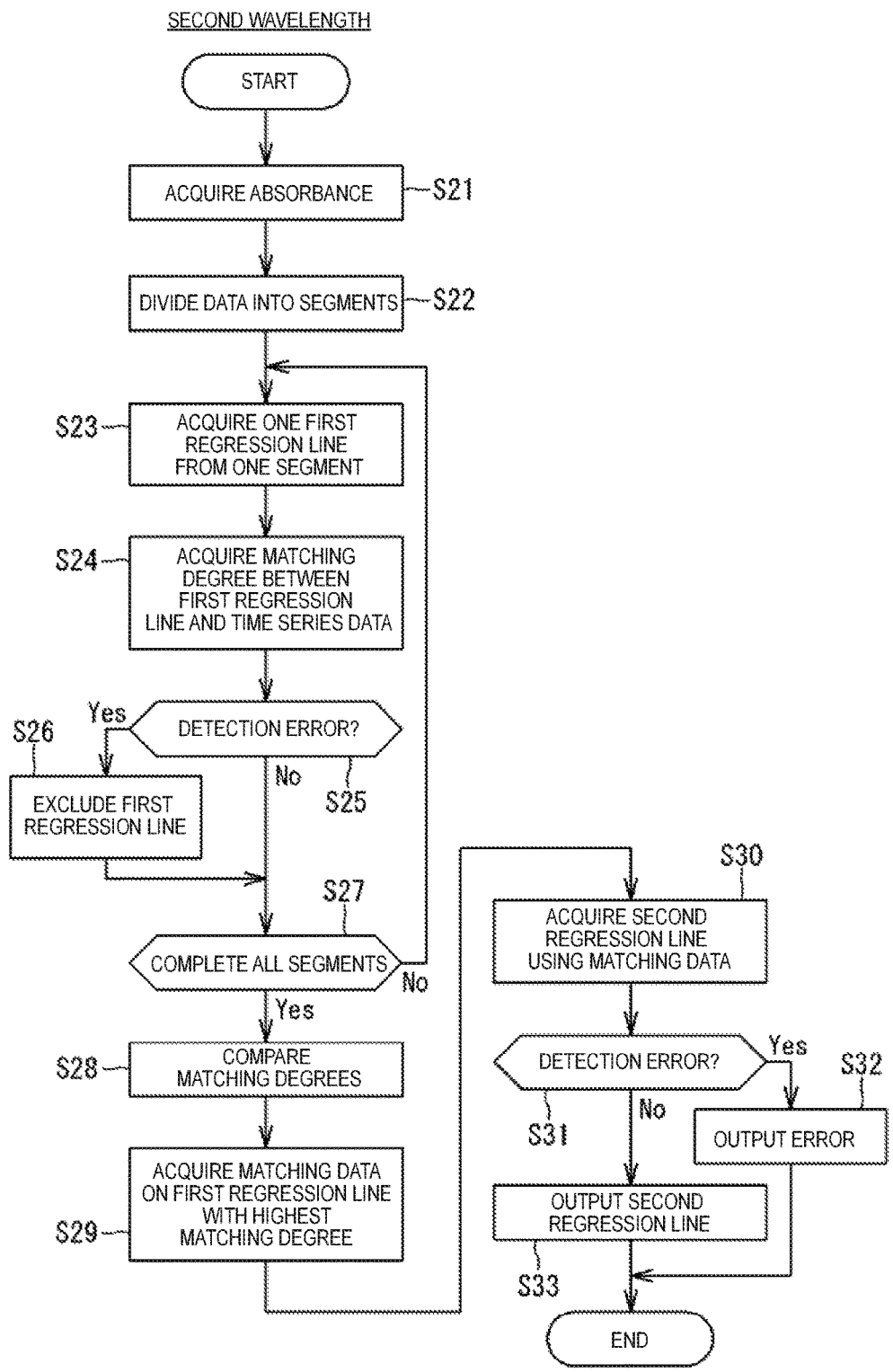
FIG. 14 is a flowchart for illustrating a process procedure of a control device.

The processings of steps S21 to S29 of FIG. 14 are the same as the processings of steps S1 to S9 of FIG. 8 described in the first embodiment. However, in the present embodiment, segments An are divided from the time series data on the second wavelength as illustrated in FIG. 11, first regression lines L1 are determined respectively for segments An. Then, first regression line L1$i$ of segment Ai with the highest matching degree with the time series data on the second wavelength is selected as illustrated in FIG. 12. A region of the time series data matching with first regression line L1$i$ is set as an "analysis target region."

Figure 13:
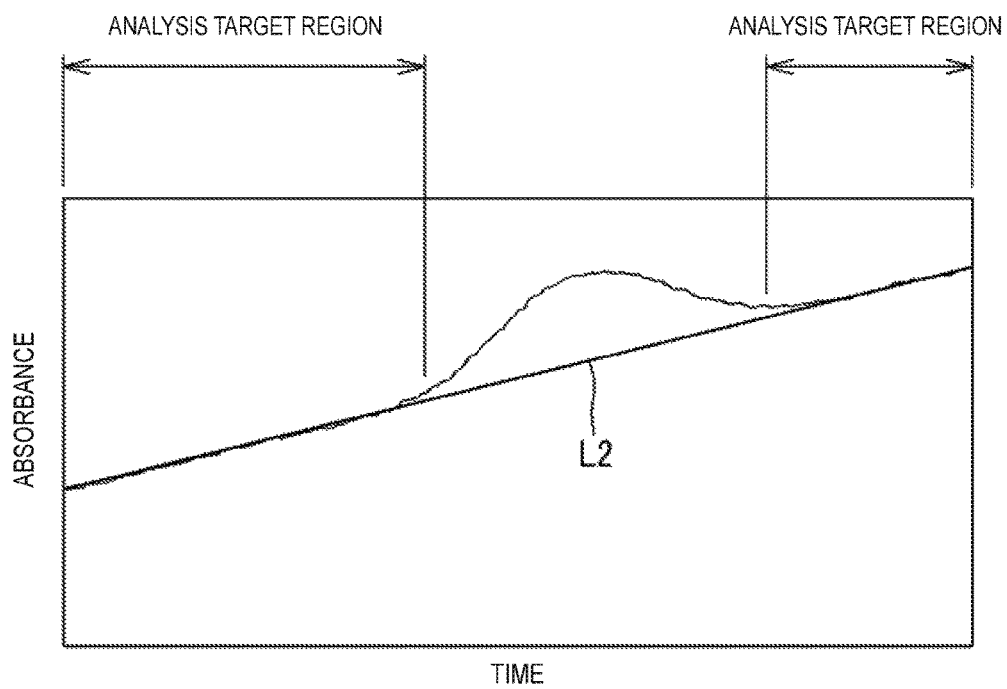
FIG. 13 is a graph for illustrating a second regression line approximating to the time series data.

The processings of steps S30 to S33 of FIG. 14 are the same as the processings of steps S12 to S15 of FIG. 8 described in the first embodiment. However, in the present embodiment, as illustrated in FIG. 13, second regression line L2 is acquired from the same time series data as the time series data from which first regression lines L1 are acquired.

The present embodiment also demonstrates the same functions and effects as those of the first embodiment. Nevertheless, while an analysis target region is determined using time series data not reflecting coagulation reaction in the first embodiment, an analysis target region is determined using time series data reflecting coagulation reaction in the second embodiment. Hence, the first embodiment can determine an analysis target region which is more accurate and is less likely to be influenced by coagulation reaction.

In the second embodiment also, curves can be used as first regression line L1 and second regression line L2. It is also possible to express first regression line L1 and second regression line L2 by a polynomial.

Moreover, in step S25 of FIG. 14, selector 22 determines whether or not time series data is a detection error on the basis of a relation between first regression line L1 and the time series data. In the case where first regression line L1 is expressed by a curve, conditions illustrated in FIGS. 15 and 16 are applicable for the detection error determination.

Figure 15:
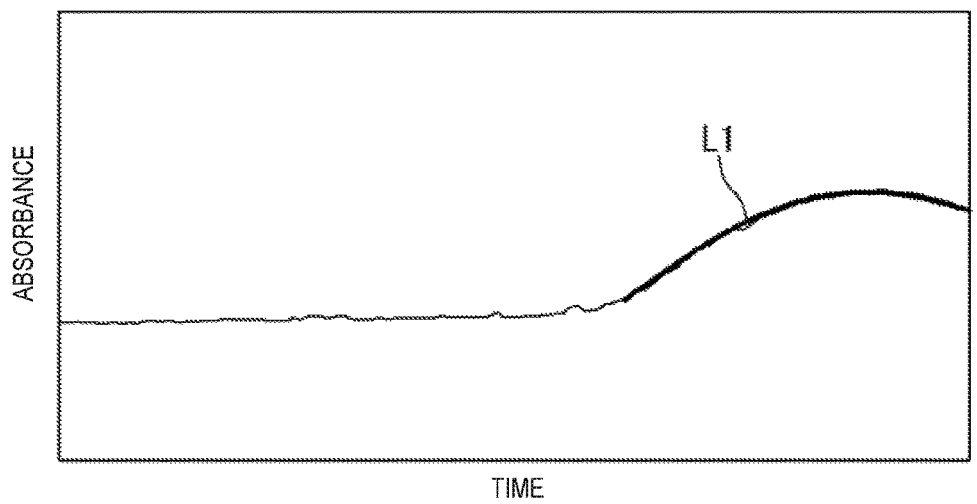
FIG. 15 is a graph for exemplifying a detection error determination condition.

The condition illustrated in FIG. 15 is a case where first regression line L1 is not monotonically increased. In a blood coagulation reaction, the absorbance hardly decreases. Hence, if first regression line L1 as illustrated in FIG. 15 is acquired, it can be determined as a detection error.

Figure 16:
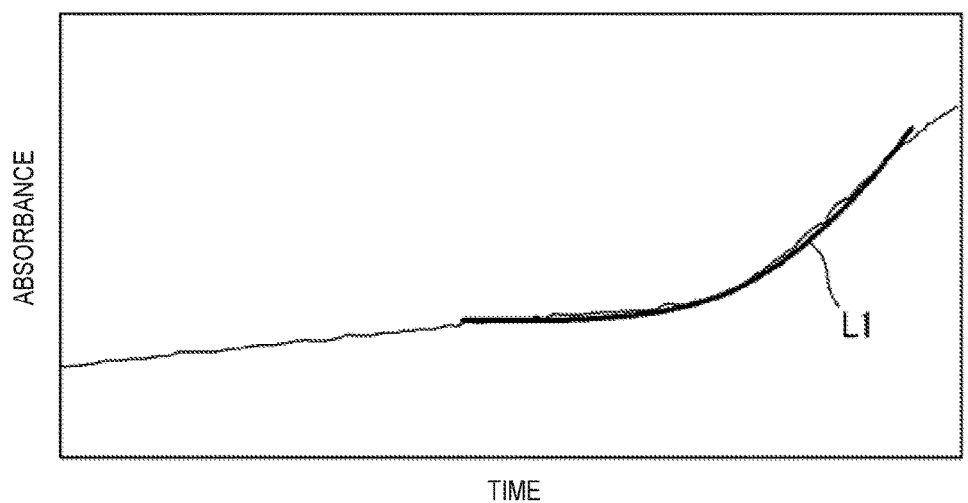
FIG. 16 is a graph for exemplifying a detection error determination condition.

The condition illustrated in FIG. 16 is a case where first regression line L1 increases in a concave shape. In a blood coagulation reaction, the initial reaction is large, and the reaction gradually becomes moderate. Hence, if first regression line L1 which increases in a concave shape is acquired, it can be determined as a detection error.

It should be understood that the above embodiments are merely illustrative in all aspects and are not restrictive. The scope of the invention is defined not by the above description but the claims, and is intended to include meaning equivalent to the claims and all modifications within the scope.

In the second embodiment, each of first regression line and second regression line is determined using time series data acquired with light at the second wavelength of 405 nm, and the second regression line is used to analyze a coagulation reaction. Nonetheless, a first regression line with the highest matching degree can also be used for the coagulation reaction analysis. However, when a second regression line is again determined from time series data on the analysis target region determined using first regression lines, a regression line more approximating to the time series data can be acquired, and a more highly reliable analysis can be performed.

Although the measurement of Factor VIII according to the synthetic substrate method has been described in the above embodiments, the invention is applicable also to measurements of other items according to the synthetic substrate method. Moreover, the invention is applicable also to items measured according to immunonephelometry.

Data segments divided from time series data may be adjusted in terms of the range (the number of data). In other words, the time-wise length of segments divided from the period of acquiring the time series data may be adjusted. For example, increasing the number of data of data segments decreases the number of segments, thereby increasing the processing efficiency. Meanwhile, an adjustment is possible to decrease the number of data of data segments if increasing the number of data of data segments results in noises in all data segments prevents appropriate determination of first regression lines.

In the above embodiments, an analysis is performed using the time series data on the absorbance. Instead, the analysis can also be performed using time series data on the amount of transmitted light. In this case, the time series data is decreased as coagulation reaction progresses, and also decreased by a noise. Further, in this case, in detection error determination in step S5 of FIG. 8, if an area of a region where the amount of transmitted light is smaller than that of first regression line L1 (positive difference region) is equal to or more than a predetermined threshold as illustrated in FIG. 9, this first regression line L1 can be determined as a detection error.

In the above embodiments, examples of the measurement of Factor VIII employing the synthetic substrate method have been described, and it is suitably applicable to a measurement where the shape of a graph obtained from time series data is a substantially linear shape. For example, it is suitably applicable to: an analysis of a measurement result of preparing a measurement specimen by mixing, as a reagent, a reagent for immunonephelometry with a sample, and then measuring the measurement specimen by immunonephelometry; and an analysis of a measurement result of preparing a measurement specimen by mixing a reagent for a synthetic substrate method with a sample, and then measuring the measurement specimen by the synthetic substrate method.

In the above embodiments, the blood coagulation analyzer has been described as a sample analyzer. Nevertheless, the invention is applicable also to other analyzers.

In this way, the embodiments described above enables a highly reliable analysis.

The invention includes other embodiments in addition to the above-described embodiments without departing from the spirit of the invention. The embodiments are to be considered in all respects as illustrative, and not restrictive. The scope of the invention is indicated by the appended claims rather than by the foregoing description. Hence, all configurations including the meaning and range within equivalent arrangements of the claims are intended to be embraced in the invention.

The invention claimed is:

1. A sample analyzer comprising:
a preparation unit configured to mix a sample and a reagent to prepare a measurement specimen;
a measurement unit comprising a light source, the measurement specimen irradiated with light from the light source to acquire time series data of an optical measurement signal over a time period during which the measurement specimen is measured;
a controller comprising a processor configured with a program to perform operations comprising:
dividing the time series data acquired by the measurement unit into data segments comprising a plurality of data points,
determining first regression lines respectively of the data segments,
calculating a matching degree between each of the first regression lines and the time series data,
selecting one of the first regression lines having a highest value of the matching degree with the time series data,
setting as an analysis target region, a region of the time series data among the time series data acquired by the measurement unit in the time period during which the measurement specimen is measured, in which ones of the time series data matches the selected first regression line,
determining a second regression line using the time series data included in the set analysis target region, and
analyzing the set analysis target region using the second regression line for an analysis target reaction in the measurement specimen.

2. The sample analyzer according to claim 1, wherein the reagent comprises one of a reagent for immunonephelometry and a reagent for a synthetic substrate method.

3. The sample analyzer according to claim 1, wherein the data segments overlap each other.

4. The sample analyzer according to claim 3, wherein the data segments overlap each other by 50% or more.

5. The sample analyzer according to claim 1, wherein the controller comprising the processor is configured with the program to perform operations such that calculating the matching degree comprises calculating the matching degree such that a difference between the first regression line and the time series data is equal to or less than a first threshold.

6. The sample analyzer according to claim 5, wherein the controller comprising the processor is configured with the program to perform operations such that calculating the matching degree comprises calculating the matching degree based on:
a number of ones of the time series data in which a difference between the first regression line and the ones of the time series data is equal to or less than the first threshold,
a length of a time including ones of the time series data in which the difference between the first regression line and the ones of the time series data is equal to or less than the first threshold, and
a percentage of a length of a time including ones of the time series data relative to the time period of acquiring the time series data in which the difference between the first regression line and the ones of the time series data is equal to or less than the first threshold.

7. The sample analyzer according to claim 1, wherein the measurement specimen is irradiated with light at different wavelengths for identical periods to acquire first time series data and second time series data on the respective wavelengths, and
the controller comprises the processor configured with the program to perform operations further comprising:
determining the first regression lines respectively of the data segments from the first time series data, calculating the matching degree between each of the first regression lines and the first time series data, selecting one of the first regression lines having a highest matching degree with the first time series data, setting as the analysis target region, a region of the first time series data in which ones of the first time series data matches the selected first regression line, determining a second regression line using the second time series data included in the analysis target region, and analyzing the set analysis target region using the second regression line for the analysis target reaction in the measurement specimen.

8. The sample analyzer according to claim 7, wherein the first time series data is acquired from a wavelength range in which the analysis target reaction is not reflected, and the second time series data is acquired from a wavelength range in which the analysis target reaction is reflected.

9. The sample analyzer according to claim 8, wherein the first time series data is acquired from a wavelength range in which the analysis target reaction does not reflect a blood coagulation reaction, the second time series data is acquired from a wavelength range in which the analysis target reaction reflects a blood coagulation reaction, and the controller comprises the processor configured with the program to perform operations such that analyzing the set analysis target region comprises analyzing the set analysis target region according to an analysis of a Factor VIII involved in blood coagulation.

10. The sample analyzer according to claim 1, wherein the controller comprises the processor configured with the program to perform operations further comprising excluding a data segment of the data segments from which the first regression line is created in a condition in which a positive or negative difference between ones of the time series data in the region of the time series data and the first regression line is equal to or more than a second threshold.

11. The sample analyzer according to claim 1, wherein the controller comprises the processor configured with the program to perform operations further comprising excluding ones of the time series data in a condition in which a width of the analysis target region is equal to or less than a third threshold.

12. The sample analyzer according to claim 1, wherein the first regression line is expressed from a zero polynomial to a binomial.

13. The sample analyzer according to claim 1, wherein the first regression line is expressed by a polynomial.

14. The sample analyzer according to claim 1, wherein the controller comprises the processor configured with the program to perform operations further comprising of adjusting a range of the data segments.

15. A sample analyzing method comprising:

mixing a sample with a reagent to prepare a measurement specimen;

irradiating the measurement specimen with light to acquire optical time series data;

dividing the acquired the time series data into data segments comprising a plurality of data points, determining first regression lines respectively of the data segments, calculating a matching degree between each of the first regression lines and the time series data, selecting one of the first regression lines having a highest value of the matching degree with the time series data, setting as an analysis target region, a region of the time series data among the time series data acquired by the measurement unit in a time period during which the measurement specimen is measured, in which ones of the time series data matches the selected first regression line, determining a second regression line using the time series data included in the set analysis target region, and analyzing the set analysis target region using the second regression line.

16. The sample analyzing method according to claim 15, wherein the reagent comprises one of a reagent for immunonephelometry and a reagent for a synthetic substrate method.

17. The sample analyzing method according to claim 15, wherein the data segments overlap each other.

18. The sample analyzing method according to claim 17, wherein the data segments overlap each other by 50% or more.

19. The sample analyzing method according to claim 15, wherein calculating the matching degree comprises calculating the matching degree such that a difference between the first regression line and the time series data is equal to or less than a first threshold.

20. A non transitory computer readable storage storing a computer program capable of being executed by a central processing unit in a sample analyzer including a measurement unit that irradiates with light a measurement specimen prepared by mixing a sample with a reagent to acquire optical time series data, the computer program enabling the central processing unit of the sample analyzer to perform functions comprising:

dividing the time series data acquired by the measurement unit into data segments comprising a plurality of data points;

determining first regression lines respectively of the data segments;

calculating a matching degree between each of the first regression lines and the time series data;

selecting one of the first regression lines having a highest value of the matching degree with the time series data;

setting as an analysis target region, a region of the time series data among the time series data acquired by the measurement unit in a time period during which the measurement specimen is measured, in which ones of the time series data matches the selected first regression line;

determining a second regression line using the time series data included in the set analysis target region; and analyzing the set analysis target region using the second regression line.

* * * * *